United States Patent [19]
Narukawa

[11] Patent Number: 4,993,646
[45] Date of Patent: Feb. 19, 1991

[54] POWDERY, GRANULAR AND CONGLOMERATE MATERIAL TREATING APPARATUS

[75] Inventor: Akira Narukawa, Yokkaichi, Japan
[73] Assignee: NGK Insulators, Ltd., Aichi, Japan
[21] Appl. No.: 414,479
[22] Filed: Sep. 29, 1989

Related U.S. Application Data

[62] Division of Ser. No. 235,560, Aug. 24, 1988, Pat. No. 4,919,342.

[51] Int. Cl.$^5$ .................................... B02C 25/00
[52] U.S. Cl. ................................. 241/37.5; 241/33; 241/101.2
[58] Field of Search .............. 241/101.2, 33, 37.5

[56] References Cited

U.S. PATENT DOCUMENTS 3,966,672 6/1976 Gaylord .......................... 241/23 X
4,784,333 11/1988 Hihalu et al. ....................... 241/5

Primary Examiner—Timothy V. Eley
Attorney, Agent, or Firm—Parkhurst, Wendel & Rossi

[57] ABSTRACT

A material treating apparatus is used for treating powdery, granular and conglomerate materials. The material treating apparatus includes a material supply apparatus for transferring the materials to a predetermined position, particularly for supplying the materials to an automatic crusher. The material treating apparatus includes a crushing system having a crushing vessel transferring unit. The material treating apparatus further includes an analysis sample transferring apparatus particularly suitable for transferring samples formed by a press to a fluorescent X-ray analyzing apparatus. The material treating apparatus includes a fluorescent X-ray analyzing system which is capable of automatically analyzing samples of various kinds. An analyzing method is carried out by the use of the above material treating apparatus. The analyzing method includes a method of vitrifying an inorganic material, which is preferably used for obtaining samples to be analyzed by the X-ray fluorescence analysis. The analyzing method further includes a method of pretreating samples for the X-ray fluorescence analysis.

4 Claims, 14 Drawing Sheets

FIG_1

FIG_2

FIG_4

FIG._5

FIG_7
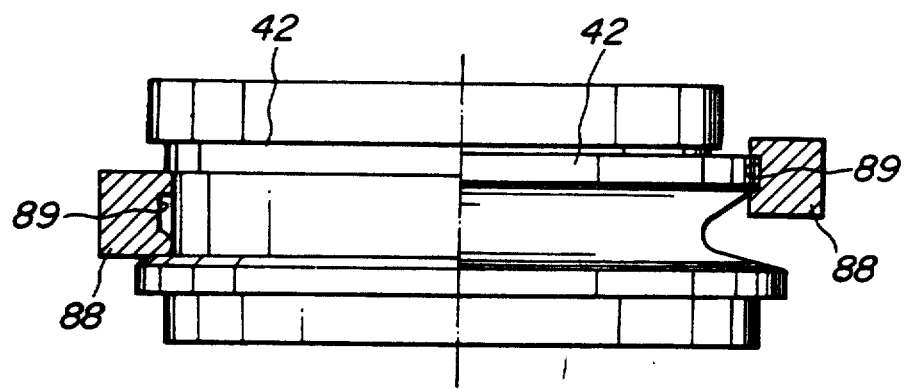

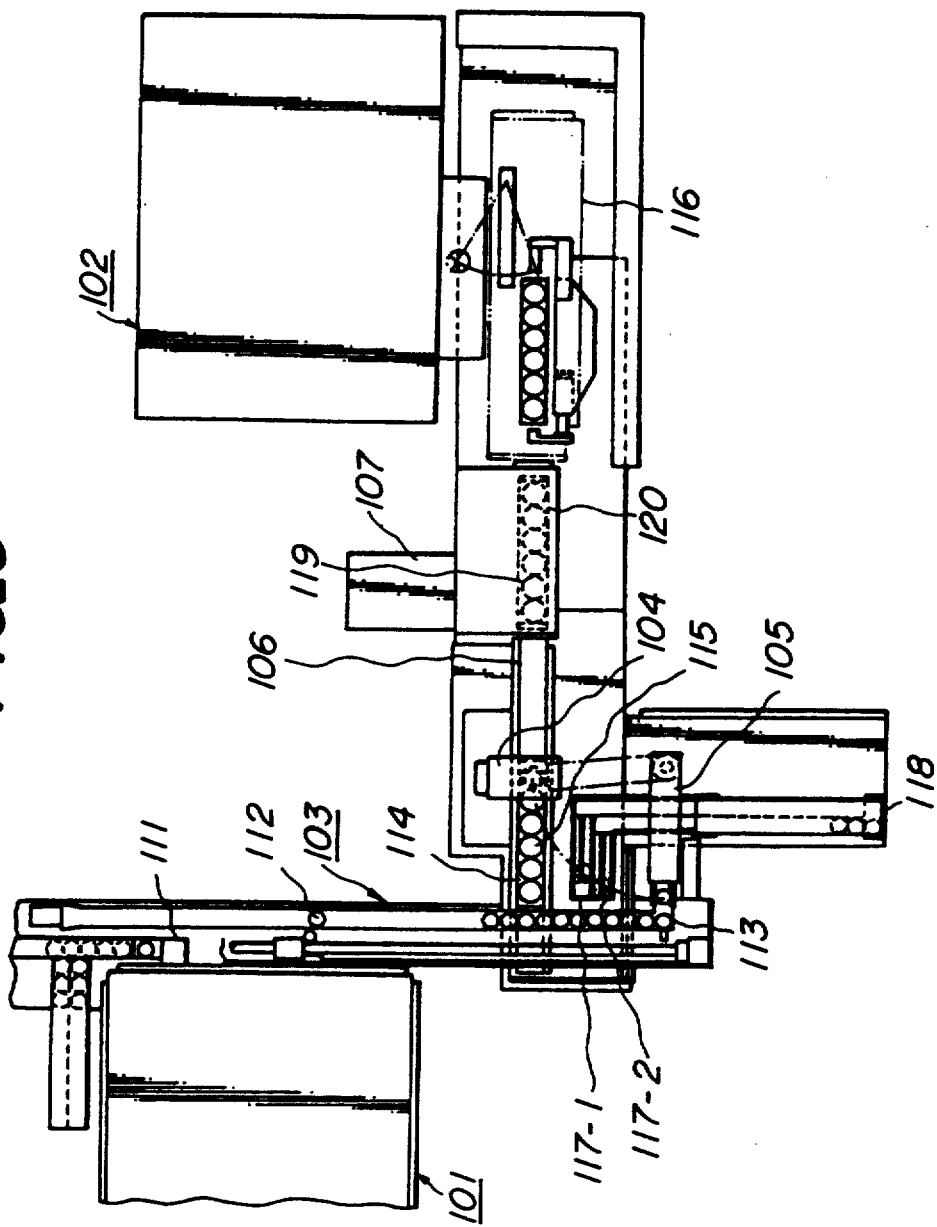

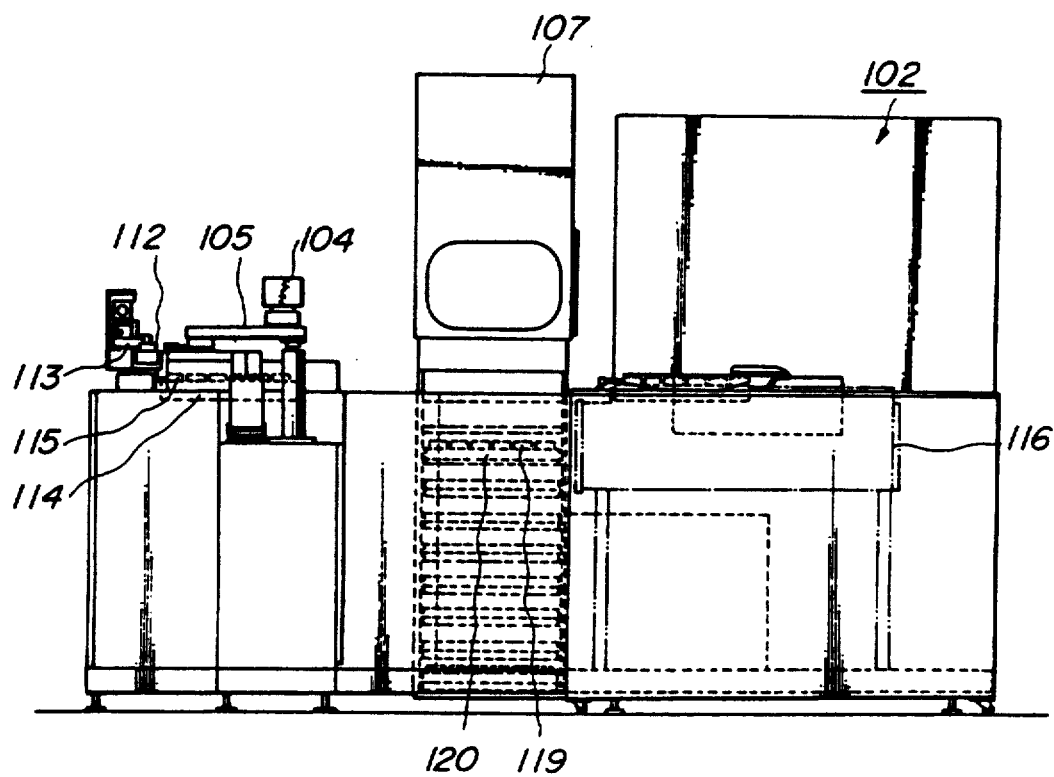
FIG_10

FIG_11a
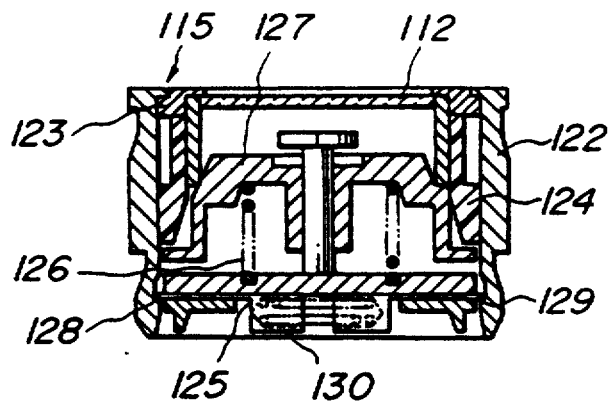
FIG_11b
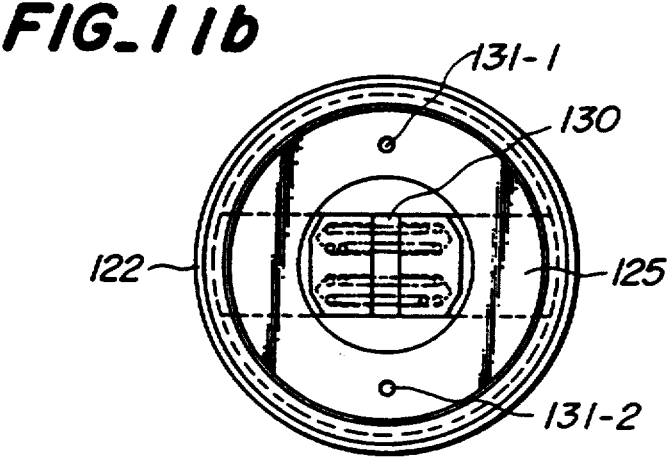
FIG_11c
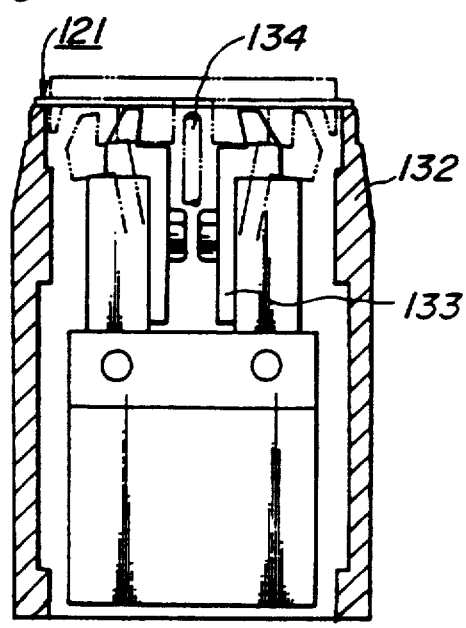

FIG_12
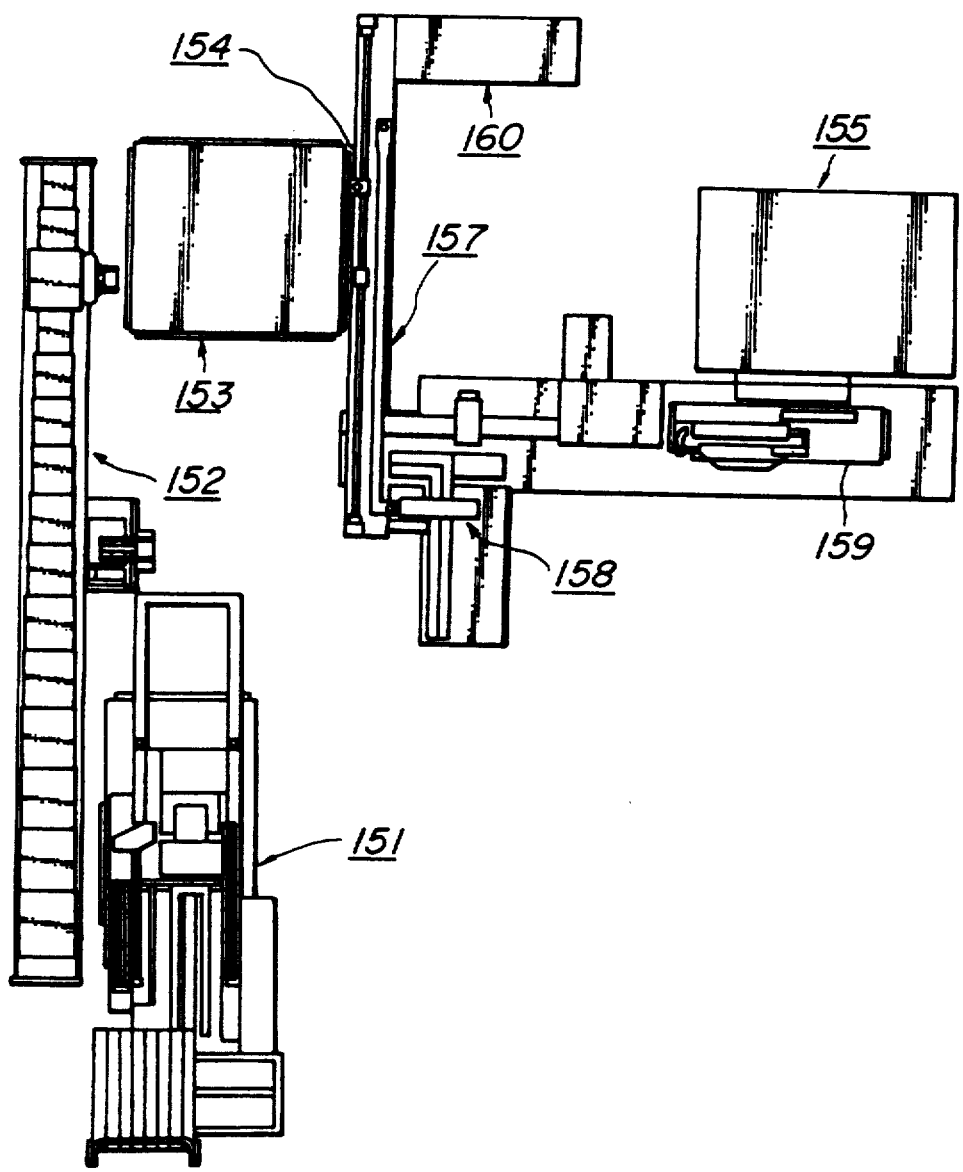

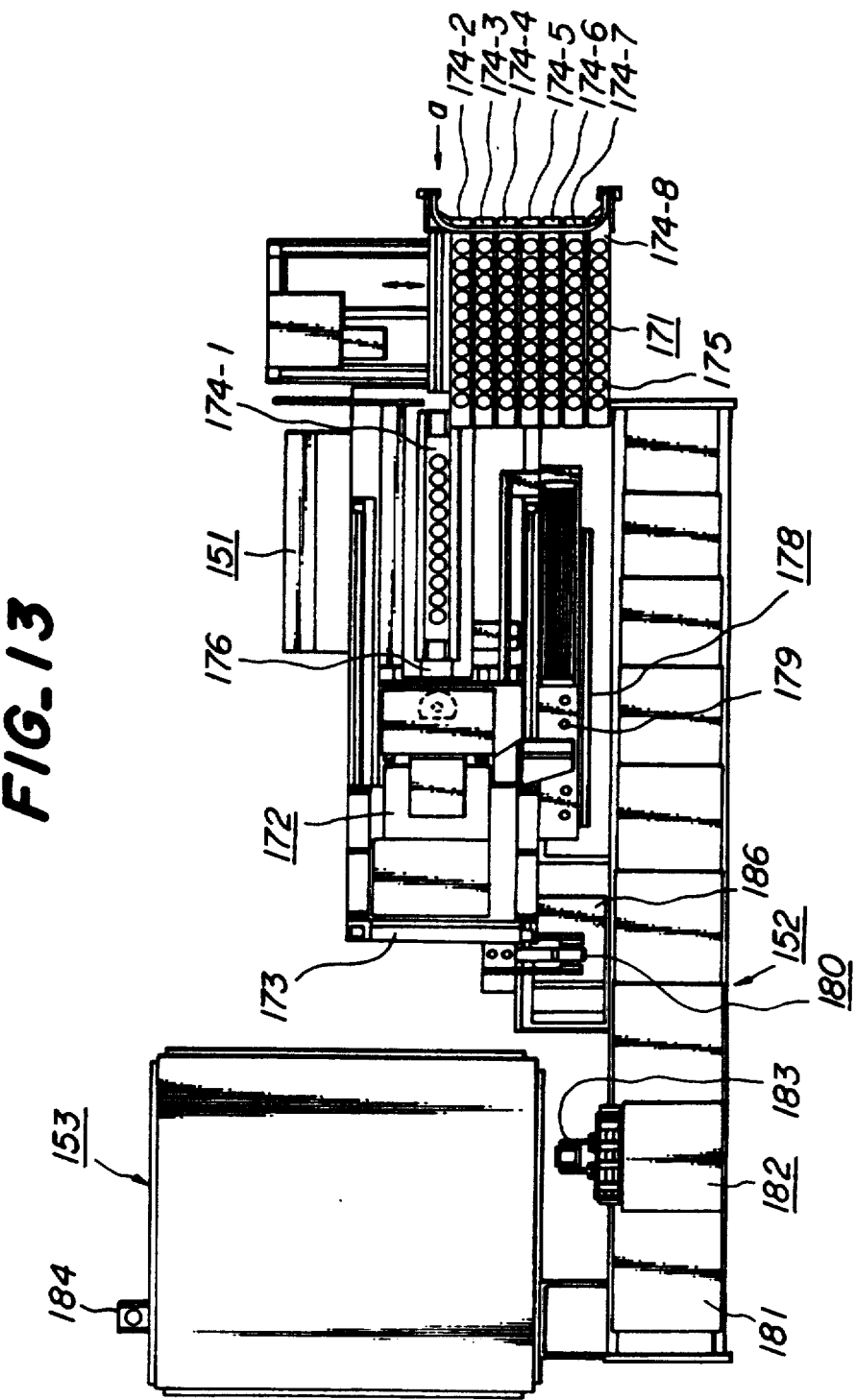
FIG._13

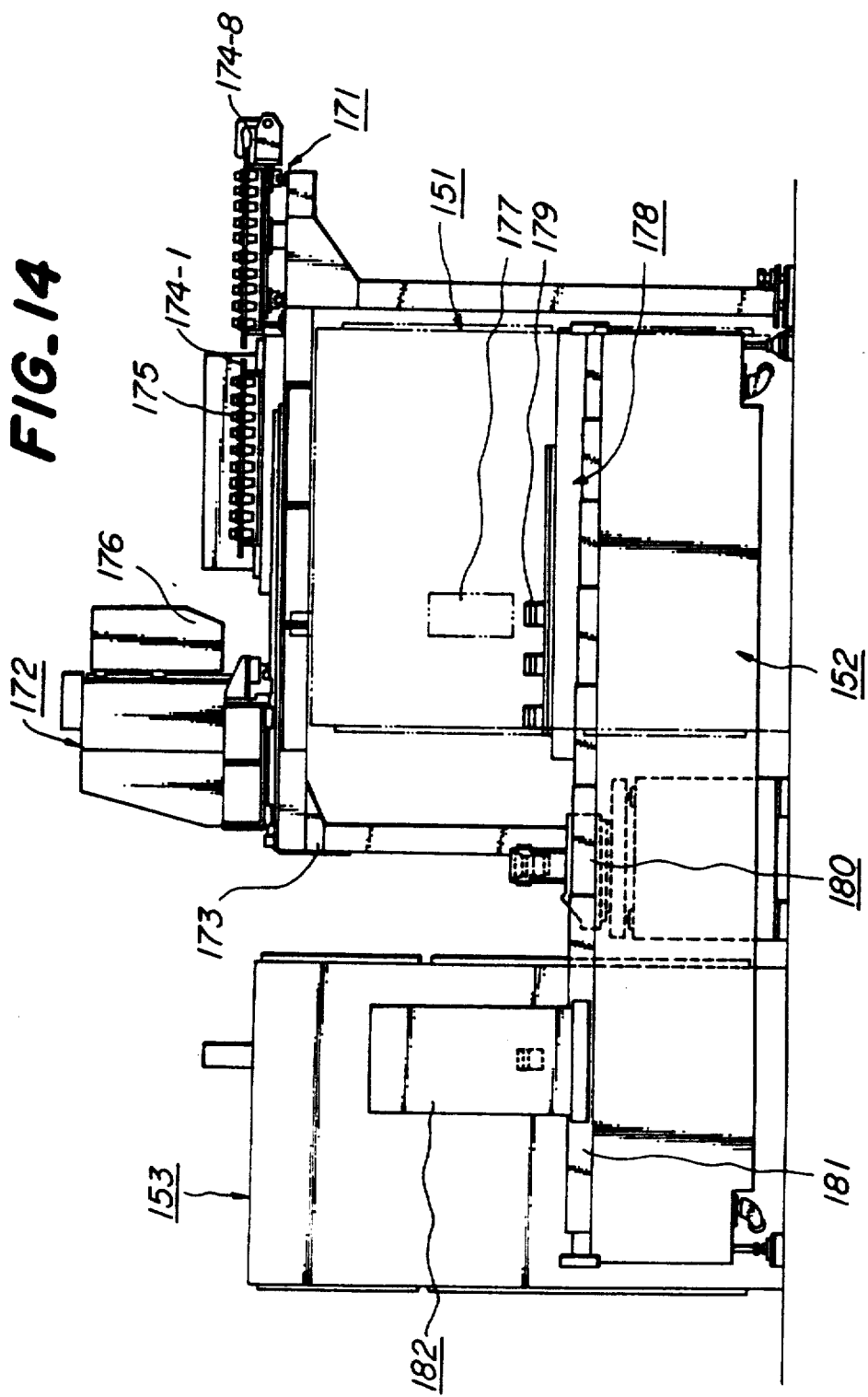

POWDERY, GRANULAR AND CONGLOMERATE MATERIAL TREATING APPARATUS

This is a Division of application Ser. No. 07/235,560 filed Aug. 24, 1988 now U.S. Pat. No. 4,919,342.

BACKGROUND OF THE INVENTION

This invention relates to an apparatus for treating powdery, granular and conglomerate materials and an analyzing method using the apparatus.

In analyzing components of various materials by a method such as the X-ray fluorescence analysis, it is necessary to pretreat the material to be analyzed.

The following four methods have been known as methods for making samples of inorganic materials.

(1) A crushing method in which a material is pulverized in order to bring the material into an appropriate condition for the analysis.
(2) A vitrifying method in which a material is added with one or a mixture of an alkali metal borate (for example, $Li_2B_4O_7$, $Li_2O.B_2O_3$ and $Na_2B_4O_7$) and heated to be vitrified.
(3) An alkali metal carbonate decomposing method in which a material is decomposed by an alkali metal carbonate.
(4) A decomposition solution method in which a material in a pressurized vessel is decomposed by a strong acid such as hydrofluoric acid to make it a solution.

The crushing method, among the above methods, is disadvantageous because if the material is at least partially crystalline, the crushed material still includes a crystal structure so that analyzed results with high accuracy could not be obtained in the X-ray fluorescence analysis due to the so-called "mineral effect". Moreover, it takes a long time to crush inorganic materials including non-oxides as components such as silicon nitride, sialon, silicon carbide and the like owing to high hardness. Moreover, there is a risk that the materials may be contaminated by a material of a vessel used for crushing. Therefore, the crushing method has been scarcely used other than in cases not requiring a high accuracy of analysis.

The alkali metal carbonate decomposing method is applicable as a pretreatment method for wet analyses, even for non-oxides. However, this method could not be used for pretreating materials for the X-ray fluorescence analysis due to the fact that decomposed and melted products are high in moisture absorption and are difficult to be removed from used vessels such as platinum dishes and the like.

The vitrifying method, using the alkali metal borate is disadvantageous because analyzing accuracy is often lowered since vitrification only partially progresses in the case of inorganic materials including non-oxides as components.

Moreover, the decomposition solution method using a strong acid requires a long time (such as 24 hours) for the decomposition. Samples obtained for the analysis are liquid which is preferable for the chemical analysis. However, it is difficult to use such liquid samples in the X-ray fluorescence analysis because of a limitation of an apparatus itself for the X-ray fluorescence analysis.

The so-called "mineral effect", which means that the grain sizes of samples detrimentally affect the accuracy of analysis of the samples, has been known. In order to avoid the mineral effect to carry out the analysis with high accuracy, it is necessary to pulverize samples in powdery, granular and conglomerate states into fine powders of the order of less than 1 $\mu$m and to form formed bodies suitable for analysis. It is preferred that the formed bodies have smooth surfaces for high accuracy analysis. Moreover, it is desired that the formed bodies are rigid and stable for a long period of time in order to facilitate the operation and automation for the analysis. The crushing to forming processes are referred to herein as "pretreatment of samples for the X-ray fluorescence analysis".

The pretreating methods for the X-ray fluorescence analysis have been known as non-addition dry crushing and non-addition wet crushing methods which are carried out in dried and wet conditions without any additions, powdery graphite added dry crushing which is carried out in a dried condition with added graphite (magazine of Japanese Metallurgy Society, vol. 36, page 648, 1972), and binder added wet crushing which is carried out in a wet condition with binders such as styrene-maleic acid copolymer or stearic acid. The powdery graphite has a lubricating effect so that it is effective as a crushing aid for promoting pulverization of samples. On the other hand, binders are effective as a forming or molding aid which gives strength to formed bodies and makes smooth surfaces of the formed bodies. Graphite is also somewhat effective as a molding aid. However, the effect of graphite as the molding aid is insufficient for disk-like formed bodies having diameters of more than 10 mm which are usually used for the X-ray fluorescence analysis.

Although the above non-addition dry crushing method is simple in operation, it is disadvantageous since crushing is sometimes insufficient, analyzing accuracy is lowered due to the mineral effect, and forming samples into disk-like bodies is difficult. The non-addition wet crushing method is disadvantageous since analyzing accuracy is lowered, forming samples into disk-like bodies is difficult and, moreover, since volatilization of solvents is needed. The powdery graphite added dry crushing method is disadvantageous since forming samples into disk-like bodies is difficult although there is no problem of lowering the analyzing accuracy due to the mineral effect. The binder added wet crushing method is disadvantageous since there is a problem of lowering the analyzing accuracy due to the mineral effect and volatilization of solvents is needed. Therefore, a pretreatment method of samples for X-ray fluorescence analysis has not been proposed, capable of obtaining formed bodies which will bring high accuracy analysis and are rigid and smooth.

In order to supply powdery, granular or conglomerate materials to predetermined positions such as crushers, weighed materials have been manually supplied from hoppers at the predetermined positions to apparatuses such as crushers.

Manual supplying requires skillful operators and obstructs automation of the entire installation line. An automated apparatus, for example, Model HSM-F36 of the HERZOG Company has been known which comprises, in the proximity of materially supplied positions, a turn table having material vessels provided along a circumference of the turn table, and introducing means for intermittently rotating the turn table.

In such an apparatus, however, the material is supplied into the hoppers with the aid of centrifugal forces caused by rotation of the material vessels driven by the introducing means. Therefore, all the materials could not be supplied into the hoppers exactly. Moreover, the turn table is disadvantageous since material is introduced into the hoppers only in a predetermined order due to the fact that the turn table performs its intermittent rotation only in connection with the material vessels.

Various crushers for a crushing samples have been known. With these crushers, crushing operation is carried out with crushing vessels made of whether the operation is, for example, tungsten carbide (WC) regardless of manual or automatic.

In this case, introduction of samples and removal of crushed samples are effected by transferring crushing vessels from the crushers to working tables. Every time kinds of samples are changed, the crushing vessels must also be transferred from the crushers to the cleaning means for cleaning the vessels. These troublesome transferring of the vessels have been manually carried out.

The vessels made of tungsten carbide or chromium steel are so heavy that the manual operation for transferring the vessels is disadvantageous to safety and efficiency. On the other hand, when organic binders are added to samples to be crushed, the binders are likely to stick to inner walls of the crushing vessels. Therefore, the attached crushed samples could not be completely removed from the crushing vessels without manual cleaning.

In various analyzing apparatuses, particularly the fluorescent X-ray analyzing apparatus, these apparatuses have been supplied with samples to be analyzed as formed bodies in predetermined shapes or accommodated in predetermined exclusive holders. In order to make such formed bodies of samples or insert samples into the holders, separate pressing apparatuses or holder loading and unloading apparatuses are needed.

In this case, the precise X-ray fluorescence analysis for various kinds of samples is accomplished by manually operating the formation of the samples and transference of the samples to the apparatuses. However it is impossible to automatically supply the samples to fluorescence X-ray analyzing apparatuses to form automatic analyzing systems. Moreover, when existing holder loading and unloading apparatuses are used, only one or two reference samples are held at a time. Therefore, such existing apparatuses could not be used for automatically analyzing various kinds of samples continuously and precise X-ray fluorescence analysis could not be realized, so that the use of the existing apparatuses is limited to particular analyses. Such a limitation of use results also from the fact that the holders are prohibitively expensive and particular. Thus, they could not be provided in large quantities.

In order to determine predetermined compositions in samples, the X-ray fluorescence analysis with X-ray has been used and various fluorescent X-ray analyzing apparatuses have been known. With such fluorescent X-ray analyzing apparatuses, in supplying a sample to the apparatus the sample must be formed in a predetermined shape and set at a predetermined position in a sample holder. Moreover, the sample must be pretreated in order to avoid the influence of physical and chemical factors of the sample on fluorescence X-ray intensity and to improve the analyzing accuracy.

For this purpose, in the case of inorganic samples such as ceramics or the like, it is required to use a crusher for crushing an inorganic raw material into predetermined grain sizes and a press for forming the crushed material into predetermined shapes. Thus, produced samples are set in the sample holder for the X-ray fluorescence analysis.

With hitherto used apparatuses, introducing the samples into the apparatuses is not reliably effected. Transferring the samples between the apparatuses and setting the samples into the apparatuses must be effected by skillful operators. Further, even with new systems partially automated with such operations, it might be ineffective, if not impossible to carry out various kinds of samples.

SUMMARY OF THE INVENTION

It is a primary object of the invention to provide an apparatus for treating powdery, granular and conglomerate materials and an analyzing method using the apparatus, which eliminate all the disadvantages of the prior art.

It is another object of the invention to provide an improved method for vitrifying inorganic materials, which eliminates all the disadvantages of the prior art and is preferably used as a method for pretreating samples for X-ray fluorescence analysis.

In order to achieve the object, a method of vitrifying an inorganic material according to the invention comprises the steps of: adding an inorganic material with an alkali metal carbonate to in an amount which is twice that of the inorganic material in weight, heating the material to decompose it and to obtain a melted product, adding the melted product with boric acid in an amount which is more than said inorganic material in weight, and heating the melted product to vitrify it.

In a preferred embodiment, in the step of adding with the alkali metal carbonate, boric acid is added to the inorganic material, the boric acid being 5–50 parts by weight relative to 100 parts by weight of the alkali metal carbonate and being less than 0.4 mol relative to 1 mole of the alkali metal carbonate.

With the above constitution, an inorganic material to be vitrified is added with a predetermined amount of an alkali metal carbonate or preferably, an alkali metal carbonate and boric acid, and decomposed in a heating process. Thereafter, the crystalline substance is vitrified by a predetermined amount of boric acid. Therefore, the mineral effect does not occur in X-ray fluorescence analysis and vitrification progresses uniformly so that good samples for analysis can be obtained in a short time.

Moreover, the vitrified substance or glass is not moisture absorptive and is easily peeled from a platinum pan or the like so that it is preferably supplied for the X-ray fluorescence analysis.

The reason why the alkali metal carbonate is twice the weight of an inorganic material to be vitrified in the decomposing process is that an alkali metal carbonate in an amount of less than twice the inorganic material makes decomposition of the material insufficient.

Moreover, the reason why the boric acid is more in weight than the inorganic material in the vitrifying process is that an amount of boric acid which is less than the inorganic material makes vitrification insufficient.

Excess alkali metal carbonate and boric acid in the vitrifying process do not cause any problem. However, in order to obtain high accuracy in the X-ray fluorescence analysis, higher X-ray intensity is preferable. For this purpose, preferable upper limits of the alkali metal carbonate is of the order of four times the inorganic material to be vitrified and the boric acid is of the order of ten times the inorganic material.

Boric acid is preferably 5–50 parts by weight relative to 100 parts by weight of the alkali metal carbonate and is preferably less than 0.4 mol relative to 1 mol of the alkali metal carbonate in the decomposing process. The reason for this is that the melted product has a flowability during decomposition so that the melted product can be easily handled. Addition of boric acid which is less than 5 parts by weight gives only less flowability making handling the melted product difficult. Addition of boric acid which is more than 50 parts by weight may cause incomplete decomposition or make the decomposition impossible.

It is a further object of the invention to provide a method of pretreating samples for the X-ray fluorescence analysis, which eliminates all the disadvantages of the prior art and obtains formed samples which are rigid and smooth to provide high accuracy analysis, and in which it is easy to automatize its operation and is most suitable for the high accuracy analysis of various kinds of samples.

In order to achieve this object, the method of pretreating a sample for X-ray fluorescence analysis according to the invention comprises the steps of: adding a sample under any powdery, granular and conglomerate conditions with powdery graphite and a forming aid simultaneously or one after another, crushing the sample under a dried condition, and press-forming the sample.

With the above constitution, the sample is added with the powdery graphite and the forming aid simultaneously or one after another, and crushed under a dried condition, thereby obtaining formed samples made of crushed materials, which are rigid, smooth and stable for long period of time. With such samples, high accuracy analysis can be accomplished by eliminating the influence of the mineral effect on the analysis accuracy.

In the case that the material is added with powdery graphite and crushed and thereafter added with a forming aid and crushed, crushing is progressed faster so that the influence of the mineral effect is more reduced. Vibration mills, attrition mills and planetary motion type mills can be preferably used as the crusher. However, the vibration mills are most preferable because of their high crushing efficiency. In the case of using a vibration mill, the crushing time is of the order of 8 minutes with simultaneous addition of the graphite and forming aid. In the case of addition step by step, the crushing time of 4 minutes per step is sufficient.

It is a further object of the invention to provide an improved material supply apparatus which eliminates all the disadvantages of the prior art and is capable of selectively introducing any materials and introducing materials automatically and exactly.

In order to achieve this object, a material supply apparatus according to the invention comprises: material vessels for receiving therein materials under any powdery, granular or conglomerate condition, material racks for accommodating therein a plurality of the material vessels, a material vessel pooling unit for holding the material racks to be driven, a material vessel transferring unit for selecting a predetermined material vessel and taking it out from said material racks and transferring it to a predetermined position, and control means for controlling operations of the material vessel pooling unit and the material vessel transferring unit.

With this arrangement, the supply of samples is carried out by controlling via control means operations of the material vessel pooling unit for driving the material rack accommodating therein sample vessels and the material vessel transferring unit for selectively transferring the material vessel, so that any materials can be automatically supplied in a predetermined order by inputting the predetermined order into the control means.

In the case that the material vessel transferring unit comprises: the grasping means, the lifter, the transfer means and the turn-over introducing means, after positioning the material vessel into a predetermined position by the grasping means, the lifter and the transfer means, the material in the vessel is completely supplied by the turn-over introducing means, thereby supplying the material more exactly.

It is an object of the invention to provide a crushing system having a crushing vessel transferring unit which eliminates all the disadvantages of the prior art, and automatizes the transference of heavy crushing vessels without automatizing manual operations which require parts such as cleaning operations.

In order to achieve this object, the crushing system having a crushing vessel transferring unit according to the invention comprises a crusher for crushing a sample in a crushing vessel, a working table for introducing the sample into the crushing vessel and removing a crushed sample from the crushing vessel, a crushing vessel cleaning unit for cleaning the crushing vessel from which the crushed sample has been removed, a crushing vessel stocker for storing cleaned crushing vessels, and a crushing vessel transferring unit for transferring the crushing vessels between the manual crusher, the working table, the crushing vessel cleaning unit and the crushing vessel stocker.

With the above arrangement, the crushing vessels are transferred between the crusher, working table, cleaning unit and stocker by means of the crushing vessel transferring unit, the introduction and removal of samples and cleaning are manually effected, while heavy crushing vessels are automatically transferred, so that crushing of samples can be carried out safely with high efficiency.

Moreover, the crushing vessel transferring unit comprises: a traverse feeding mechanism capable of coarse movements and fine movements for positioning, a lifting mechanism for raising and lowering the crushing vessels, a clamping mechanism for clamping the crushing vessel, a tilting mechanism for tilting the crushing vessel, and a control board for instructing operations of the above mechanisms. Therefore, the traverse feeding mechanism capable of rough and fine movements enables the crushing vessels to be exactly positioned at the crusher, working table, cleaning bath and turn table. The crushing vessel clamped in the clamping mechanism can be tilted during cleaning by the tilting mechanism, so that the crushing vessel is cleaned by both hands of an operator, thereby shortening the time required for cleaning and effecting the cleaning with high efficiency.

It is another object of the invention to provide an improved analysis sample transferring apparatus which eliminates all the disadvantages of the prior art and which enables a system to be automatized and preferably supplies various kinds of samples successively to an analyzing apparatus.

It is a further object of the invention to provide an analysis sample transferring apparatus which is inexpensive and does not detrimentally affect the accuracy of X ray fluorescence analysis by providing a holder with clamp means which is a modification of existing clamp means.

For this object, the analysis sample transferring apparatus according to the invention comprises: a formed sample transferring unit for transferring and temporarily storing formed samples, a formed sample loading and unloading unit for loading and unloading a formed sample into and out of a predetermined holder and loading and unloading the loaded and unloaded holder into and out of a holder tray, a formed sample delivery unit for transferring the formed samples between the formed sample transferring unit and the formed sample loading and unloading unit, a holder tray transferring unit for transferring the holder tray to a predetermined position, and a reference sample storing and lifting unit.

With the above arrangement, a formed analysis sample can be loaded into and unloaded out of the holder in a predetermined timing, and the holder can be transferred to a predetermined analyzing apparatus by the holder tray, so that the analysis sample can be automatically transferred to the predetermined analyzing apparatus without requiring manual operations. Moreover, a reference sample storing and lifting unit capable of storing various kinds of reference samples is added to the holder tray transferring unit, calibration curves or calibration of analyzing apparatus during the analysis of various kinds of samples. Further, formed samples can be loaded into and unloaded out of the holder, so that samples of various kinds are analyzed with high accuracy.

It is an object of the invention to provide a fluorescent X-ray analyzing system which eliminates all the disadvantages of the prior art and which is capable of handling samples of various kinds and does not require any manual operation for transferring samples between respective units and for setting the samples in the respective units so that manual operations can be completely deleted.

For the object, the fluorescent X-ray analyzing system according to the invention comprises: an automatic crusher for selecting a predetermined sample from various samples and crushing the sample into a predetermined size, a crushed sample transferring unit for transferring the crushed sample, an automatic press for forming the sample transferred by the crushed sample transferring unit into a predetermined shape, a formed sample supply unit for supplying the formed sample to a next step, a fluorescent X-ray analyzing apparatus for determining amounts of elements in the supplied sample, and control means for controlling respective operations of the automatic crusher, the crushed sample transferring unit, the automatic press, the formed sample supply unit and the fluorescent X-ray analyzing apparatus.

With the above arrangement, the crushed sample transferring unit and the formed sample supply unit connect between the automatic crusher, automatic press and fluorescent X-ray analyzing apparatus, and operations of these components are controlled by the control means. Therefore, automatization of the system can be accomplished and power can be saved.

Moreover, samples of various kinds are continuously automatically analyzed without contamination between the samples by the use of the automatic crusher for selectively crushing the samples of various kinds, preferably comprising the sample rack, sample supply unit and cleaning unit and securely cleaning the crushing vessel.

Further, when the fluorescent X-ray analyzing apparatus comprises the sample transferring unit, the holder loading and unloading unit and the sample loader, the formed samples are automatically supplied to the fluorescent X-ray analyzing apparatus in a preferable manner.

In order that the invention may be more clearly understood, preferred embodiments will be described, by way of example, with reference to the accompanying drawings.

BRIEF DESCRIPTION OF THE DRAWINGS

FIG. 7 is a schematic view for explaining a clamping method for a crushing vessel;

FIG. 9 is a plan view illustrating one example of an analysis sample transferring unit according to the invention together with a fluorescent X-ray analyzing apparatus;

FIG. 10 is a front elevation illustrating the analysis sample transferring unit and the analyzing apparatus shown in FIG. 9;

FIG. 11a is a sectional view of a holder to be used in the analysis sample transferring unit shown in FIG. 9;

FIG. 11b is a bottom plan view of the holder shown in FIG. 11a;

FIG. 11c is a sectional view of a clamp built-in spindle used in the analysis sample transferring unit shown in FIG. 9;

FIG. 12 is a plan view illustrating one example of a fluorescent X-ray analyzing system;

FIG. 13 is a plan view illustrating one example of an upper construction of an automatic crusher used in the system shown in FIG. 12; and FIG. 14 is a side view of the upper construction of the automatic crusher shown in FIG. 13.

DESCRIPTION OF THE PREFERRED EMBODIMENTS

Figure 1:
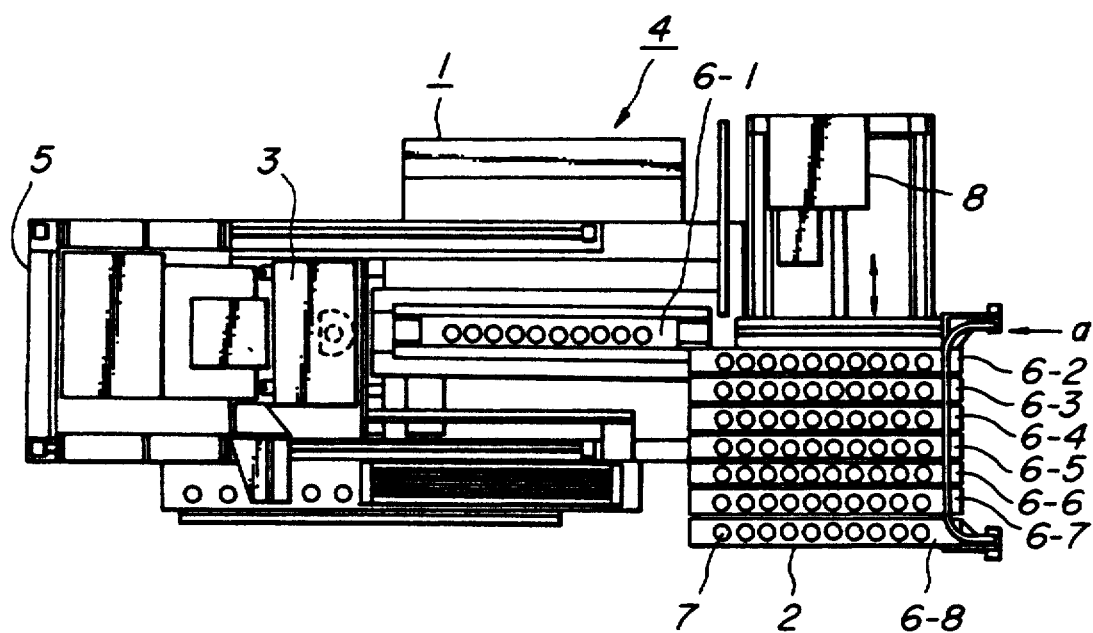
FIG. 1 is a plan view illustrating one example of a material supply apparatus according to the invention together with an automatic crusher.

The vitrifying method for preparing samples to be analyzed according to the invention will be explained as one example hereinafter referring to a case that an inorganic material including silicon nitride is the inorganic material to be vitrified. The inorganic material including silicon nitride is referred to hereinafter simply as "silicon nitride". First, powder of the silicon nitride or coarse grains of sintered silicon nitride (for example 3 mm, 5 mm and the like) are prepared by weighing. Lithium carbonate or the like as an alkali metal carbonate, and boric acid if required are prepared by weighing. The prepared silicon nitride, lithium carbonate and boric acid are mixed in a dish made of platinum-gold alloy and then progressively heated by a Bunsen burner and if required, a Méker burner. In this case, the heating is started from a low temperature and the heating power is progressively increased to effect a decomposition resulting from the heating. Such a heating and decomposing process is completed at an instant when bubbles of $CO_2$, $N_2$ and the like generating from the mixture disappear.

After the mixture is cooled by leaving it in the atmosphere, the mixture is added with a predetermined amount of boric acid and heated by the Méker burner. The heating is started from low temperature and the heating power is progressively increased. At the last stage of the heating, the mixture is intensively heated at about 1,000° C. to achieve vitrification of the mixture. In the vitrifying process, the melted mixture is intensively heated while the mixture is rocked. After the vitrification, compressed air is jetted onto the dish of the platinum-gold alloy to forcedly cool the mixture. Thereafter, the melted mixture is stripped from the dish. In order to prevent the detrimental influence by segregation of the vitrified products, the melted products are pressed after grinding to obtain formed bodies for the X-ray fluorescence analysis. It takes about two hours from time of the preparation of the sample to the X-ray fluorescence analysis.

If required, sodium carbonate or potassium carbonate may be used as the metal carbonate instead of the lithium carbonate. Moreover, other dishes may be used such as a crucible made of platinum-gold alloy, platinum or graphite, a dish of platinum. Actual examples will be explained hereinafter.

In order to carry out the vitrifying method according to the invention, silicon nitride samples No. 1-7 were prepared which were different in the amount of silicon nitride they contained and included lithium carbonate and boric acid of the respective percentages shown in Table 1. Decomposing states in the heating and decomposing process and vitrified states in the vitrified process were reviewed. Those which were completely decomposed and whose glasses are transparent and easily stripped were indicated by . Although completely decomposed and glasses samples were easily stripped, those which were somewhat difficult to be stripped are indicated by . Those which were incompletely decomposed and vitrified are indicated by x in Table 1.

TABLE 1

|  | No. | Silicon nitride sample (g) | Percentage of silicon nitride (wt %) | Lithium carbonate (g) | Boric acid (g) When decomposed | Boric acid (g) When vitrified | Estimate Decomposition | Estimate Vitrification |
|---|---|---|---|---|---|---|---|---|
| Present invention | 1 | 2 | 90 | 4.0 | 0 | 2 |  |  |
|  | 2 | 2 | 85 | 4.0 | 0.2 | 2 |  |  |
|  | 3 | 2 | 90 | 5.0 | 0.5 | 5 |  |  |
|  | 4 | 2 | 99 | 5.0 | 0.5 | 10 |  |  |
|  | 5 | 2 | 75 | 8.0 | 2.0 | 20 |  |  |
|  | 6 | 2 | 55 | 5.0 | 2.5 | 5 |  |  |
|  | 7 | 2 | 30 | 4.0 | 0.2 | 2 |  |  |
| Comparative example | 8 | 2 | 80 | 2.0 | 0.2 | 2 | X | X |
|  | 9 | 2 | 90 | 5.0 | 0.5 | 1 |  | X |
|  | 10 | 2 | 90 | 2.0 | 0.2 | 1 | X | X |
|  | 11 | 2 | 80 | 2.0 | 2.0 | 2 | X | X |

TABLE 2

|  | No. | Silicon carbide sample (g) | Percentage of silicon carbide (wt %) | Lithium carbonate (g) | Boric acid (g) When decomposed | Boric acid (g) When vitrified | Estimate Decomposition | Estimate Vitrification |
|---|---|---|---|---|---|---|---|---|
| Present invention | 21 | 2 | 90 | 4.0 | 0 | 2 |  |  |
|  | 22 | 2 | 85 | 4.0 | 0.2 | 2 |  |  |
|  | 23 | 2 | 98 | 5.0 | 0.5 | 5 |  |  |
|  | 24 | 2 | 80 | 5.0 | 0.5 | 10 |  |  |
|  | 25 | 2 | 55 | 5.0 | 2.5 | 5 |  |  |
|  | 26 | 2 | 30 | 4.0 | 0.2 | 2 |  |  |
| Comparative example | 27 | 2 | 90 | 2.0 | 0.2 | 2 | X | X |
|  | 28 | 2 | 95 | 5.0 | 0.5 | 1 |  | X |
|  | 29 | 2 | 95 | 2.0 | 2.0 | 2 | X | X |

Moreover, silicon carbide samples Nos. 21-26 were prepared and tested which were different in the amount of silicon carbide they contained. Results are shown in Table 2, which are estimated in the same manner as in Table 1. Among these samples, the silicon nitride sample No. 4 and the silicon carbide sample No. 23 are powdery raw material, while the other samples are coarse grains of sintered materials.

Silicon nitride samples Nos. 8-11 and silicon carbide samples Nos. 27-29 were separately prepared and included lithium carbonate or boric acid whose amounts were out of the range according to the invention. These comparative samples were vitrified. With the silicon nitride samples Nos. 1-11 and the silicon carbide samples Nos. 21-29, the respective ten samples were vitrified and estimated.

As can be seen from the results in Tables 1 and 2, the samples Nos. 1-7 and Nos. 21-26 are substantially good in decomposition and vitrification. Amounts of lithium carbonate in the heating and decomposing processes in these samples are more than twice that of the silicon nitride samples or silicon carbide samples. Amounts of boric acid in the vitrifying processes in these samples are equal to or more than those of the silicon nitride samples or silicon carbide samples according to the invention. On the other hand, decomposition and vitrification are insufficient with the comparative samples Nos. 8-11 and Nos. 27-29 which do not fulfil the above conditions according to the invention.

Moreover, ten samples were prepared by crushing sintered silicon nitride without vitrification. Further, ten samples were prepared by crushing after vitrification according to the manner as in sample No. 3 in Table 1 of the invention. These samples were subjected to the X-ray fluorescence analysis to review calibration curves (relations between intensities of X-ray fluorescence analysis and concentrations of the respective components).

Table 3 indicates accuracies of the calibration curves of the respective components with the aid of the following equation:

$$\sigma = \sqrt{\frac{\Sigma(C_{chem} - C_{x\text{-}ray})^2}{n - k}}$$

$\sigma$: accuracy of calibration
$C_{chem}$: analyzed value by chemical analysis wt %
$C_{x\text{-}ray}$: analyzed value by X-ray fluorescence analysis wt %
n: the number of reference samples used for obtaining calibration curves
k: the number of parameters used in presumption for regression equations Moreover, accuracies of calibration curves with silicon carbide crystals were measured in the same manner as described above, the results of which are shown in Table 4. In both cases of silicon nitride and silicon carbide, accuracies of analyzed values by the X-ray fluorescence analysis with samples vitrified according to the invention are one figure or place higher than those with samples crushed without being vitrified.

TABLE 3

| Analyzed component | With vitrification (third embodiment) (wt %) | Without vitrification (crushing method) (wt %) |
|---|---|---|
| Si | 0.04 | 0.8 |
| Al | 0.008 | 0.05 |
| Fe | 0.02 | 0.02 |
| Ti | 0.002 | 0.002 |
| Ca | 0.001 | 0.001 |
| Mg | 0.02 | 0.1 |
| K | 0.002 | 0.002 |
| Na | 0.002 | 0.002 |
| Sr | 0.01 | 0.1 |
| Ce | 0.02 | 0.3 |
| Zr | 0.02 | 0.4 |
| Y | 0.02 | 0.6 |

TABLE 4

| Analyzed component | With vitrification (wt %) | Without vitrification (crushing method) (wt %) |
|---|---|---|
| Si | 0.04 | 0.9 |
| Al | 0.002 | 0.03 |
| Fe | 0.01 | 0.01 |
| Ti | 0.002 | 0.002 |
| Cr | 0.008 | 0.009 |

The invention is not limited to the embodiments described above and various changes and modifications may be made in the invention. For example, although the above embodiments have been explained with silicon nitride and silicon carbide, the invention is applicable to usual inorganic materials such as sintered ceramics, glasses, powders and the like.

Moreover, although the above embodiments have been explained in consideration of the X-ray fluorescence analysis, it is possible to use them as samples for a wet analysis such as atomic absorption spectrometry, inductively coupled plasma atomic emission analysis and the like by solving vitrified products or their crushed materials in an acid.

As can be seen from the above explanation, an inorganic material is added with a predetermined amount of alkali metal carbonate, preferably alkali metal carbonate and boric acid and decomposed in the heating and decomposing process. Thereafter the mixture is vitrified with a predetermined amount of boric acid. Therefore, when the sample is analyzed by the X-ray fluorescence analysis, no mineral effect occurs so that high accuracy analysis can be effected in comparison with the crushing method. In the X-ray fluorescence analysis using samples vitrified according to the invention, the time required for the analysis can be shortened to about one tenth of that in the chemical analysis.

The inorganic material vitrifying method according to the invention is advantageously used for producing or pretreating samples for the X-ray fluorescence analysis as a high speed analysis so that the industrial value of the invention is inestimable.

A method of pretreating samples or specimens to be analyzed according to the method of the invention will be explained hereinafter. However, samples or specimens to be analyzed according to the method of the invention may be, of course, pretreated by any other methods explained herein. An actual embodiment will be explained.

A granular feldspar specimen having sides less than 10 mm, powdery graphite and styrene-maleic acid copolymer were prepared and weighed to obtain compositions shown in Table 4. Thereafter, the weighed granular feldspar specimen, powdery graphite and styrene-maleic acid copolymer were simultaneously introduced into a vessel made of tungsten carbide and crushed or pulverized in a dried condition by the use of a vibrating mill for about eight minutes. Then the crushed materials were pressed in dies as material holding means or without dies at a forming pressure of 30 tons to obtain disk-like formed bodies 38 mm in diameter to be analyzed by the X-ray fluorescence analysis.

At the same time, disk-like formed bodies were prepared in the same manner described above with the exception of the addition of the powdery graphite as comparison samples. Moreover, other formed bodies were prepared as samples of the prior art, in which the powdery graphite was added without adding the styrene-maleic acid copolymer. In other formed bodies as samples of the prior art, crushing was effected without adding the powdery graphite.

The material or formed body holding means were rings or cups for receiving the formed bodies in order to facilitate the forming operation and handling of the bodies which were poor in moldability.

Steel rings, synthetic resin rings, aluminum rings, aluminum cups and the like are preferably used for this purpose. However, the steel rings are the most preferable because they are able to be repeatedly used and to retain deformation of the formed bodies to lesser extent.

Although the diameters of the formed bodies are 38 mm in the above embodiment, the diameters are not limited to this value. For example, if the amounts of samples are small, dies having smaller diameters may be used to obtain smaller diameters formed bodies. Formed bodies having small diameter of the order of 10 mm can be supplied to the X-ray fluorescence analysis according to the invention.

Although a forming pressure of 30 tons (about 2.6 ton/cm$^2$) are used in the above embodiment, the forming pressure is not limited to this value. The forming pressure requires only to be able to give the formed bodies the strength sufficient to be supplied to the X-ray fluorescence analysis and is preferably 0.2-5 ton/cm$^2$.

The formed bodies obtained were compared with states of the bodies and measured accuracies of SiO$_2$ calibration curves by X-ray fluorescence analysis. The states of the formed bodies were classified as follows those designated by    which were strong superior in surface smoothness and very stable for long periods of time, those designated by    which did not have cracks but were not very good in surface smoothness or less stable for long periods, those designated by Δ which were poor in accuracy owing to partial cracks but were able to be analyzed by the X-ray fluorescence analysis, and those designated by x which were not obtained in formed bodies. The accuracies $\pi$ of calibration curves were obtained by using reference samples according to the equation (1) described above. The results are shown in Table 5.

according to the invention, the preparation of samples is completed in a short period of time. Furthermore, a suitable formed body holding means makes it easy for automatically handling the formed bodies so that all the operations of the X-ray fluorescence analysis, including the pretreatment, can be automated with ease.

Figure 2:
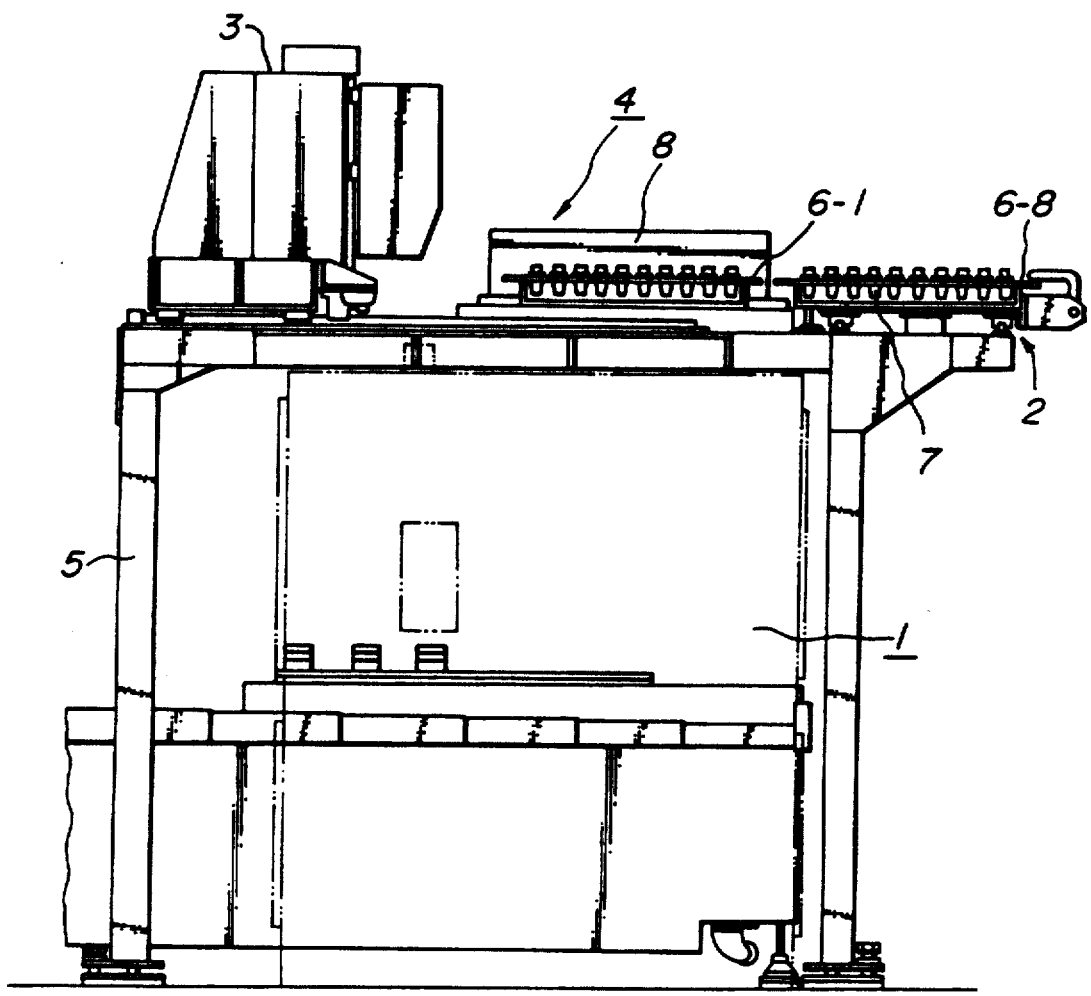
FIG. 2 is a front elevation illustrating the material supply apparatus and the automatic crusher shown in FIG. 1.

FIGS. 1 and 2 illustrate in plan and front views one example of the material supply apparatus according to the invention.

In this embodiment, above an automatic crusher 1 and on a base 5 a material supply unit 4 is provided comprising a material vessel pooling unit 2 and a material vessel transferring unit 3 so that particular materials are selected from various kinds of materials and introduced into the automatic crusher 1. Material racks 6-1 to 6-8 of the material vessel pooling unit 2 receive ten material vessels 7, respectively. There are totally (8 × 10) material vessels 7. Before starting the operation, positions and kinds of the eighty materials are inputted into a control means 8, on the basis of which inputted data the materials are supplied. The material vessel pooling unit 2 is able to move in both directions shown by an arrow so that a rack or rack 6-1 in this embodiment positioned at a rack moving position, a, is transferred to a material introducing position shown in the drawing. The materials in the material vessels 7 at the material introducing position are held and transferred

TABLE 5

| Sample No. | Present invention | | | | | | | Comparative example Crushed in dry with binder | Prior art | | | Crushed in dry with binder |
|---|---|---|---|---|---|---|---|---|---|---|---|---|
| | 1 | 2 | 3 | 4 | 5 | 6 | 7 | 11 | Crushed in dry with graphite | | | 15 |
| | | | | | | | | | 12 | 13 | 14 | |
| Amount of feldspar sample (g) | 5.0 | 5.0 | 5.0 | 5.0 | 5.0 | 5.0 | 5.0 | 5.0 | 5.0 | 5.0 | 5.0 | 5.0 |
| Added amount of graphite (g) | 0.25 | 0.25 | 0.5 | 1.0 | 1.5 | 2.0 | 2.0 | — | 0.5 | 1.0 | 1.5 | — |
| Percentage to sample (wt %) | 1 | 5 | 10 | 20 | 30 | 40 | 40 | — | 10 | 20 | 30 | — |
| Styrene-maleic acid copolymer (g) | 0.25 | 0.5 | 1.0 | 1.0 | 1.5 | 1.5 | 2.0 | 0.5 | — | — | — | 0.5 |
| Percentage to sample (wt %) | 5 | 10 | 20 | 20 | 30 | 30 | 40 | 10 | — | — | — | 10 |
| Formed body supporting means | Steel ring | Without using | Without using | Without using | Without using | Without using | Without using | Without using | Steel ring | Aluminum ring | Aluminum cup | Without using |
| State of formed body | | | | | | | | X | X | X | Δ | |
| Accuracy of SiO$_2$ calibration of wt % (Determination range 50-85 wt %) | 0.11 | 0.017 | 0.027 | 0.046 | 0.034 | 0.25 | 0.29 | 0.55 | — | — | 0.32 | 0.36 |

As can be seen from the results of Table 5, the samples subjected to the pretreatment according to the invention are superior in the state of formed bodies and make it possible to carry out correct measurements.

Moreover, the same measurement was effected with other silicates. It has been found that the pretreatment method can be applicable to almost all the silicates. They are pulverized to average grain diameters of about 0.5 μm in a few minutes and disk-like formed bodies under good conditions are easily obtained.

As can be seen from the above explanation, the mineral effect of samples is remarkably reduced to make the analysis with high accuracy by adding the forming aid such as powdery graphite and styrene-maleic acid copolymer to the sample simultaneously or one after another and crushing them in a dried condition. Moreover, as the samples are crushed in a dried condition by the material supply unit 4 in a predetermined order so as to be supplied into a material introducing opening of the automatic crusher 1.

Figure 3:
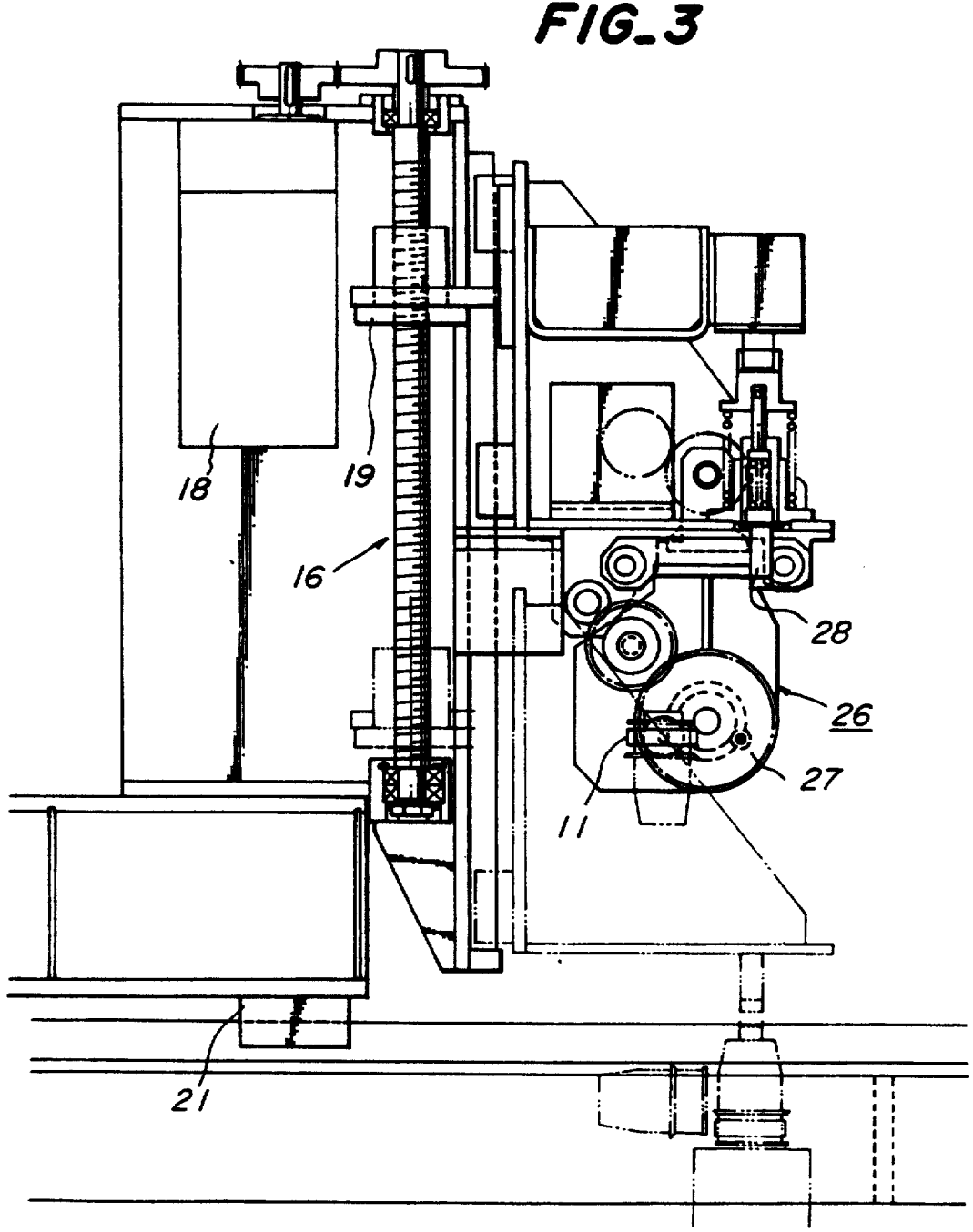
FIG. 3 is a front elevation of a material vessel transferring unit in the material supply apparatus shown in FIG. 1.
Figure 4:
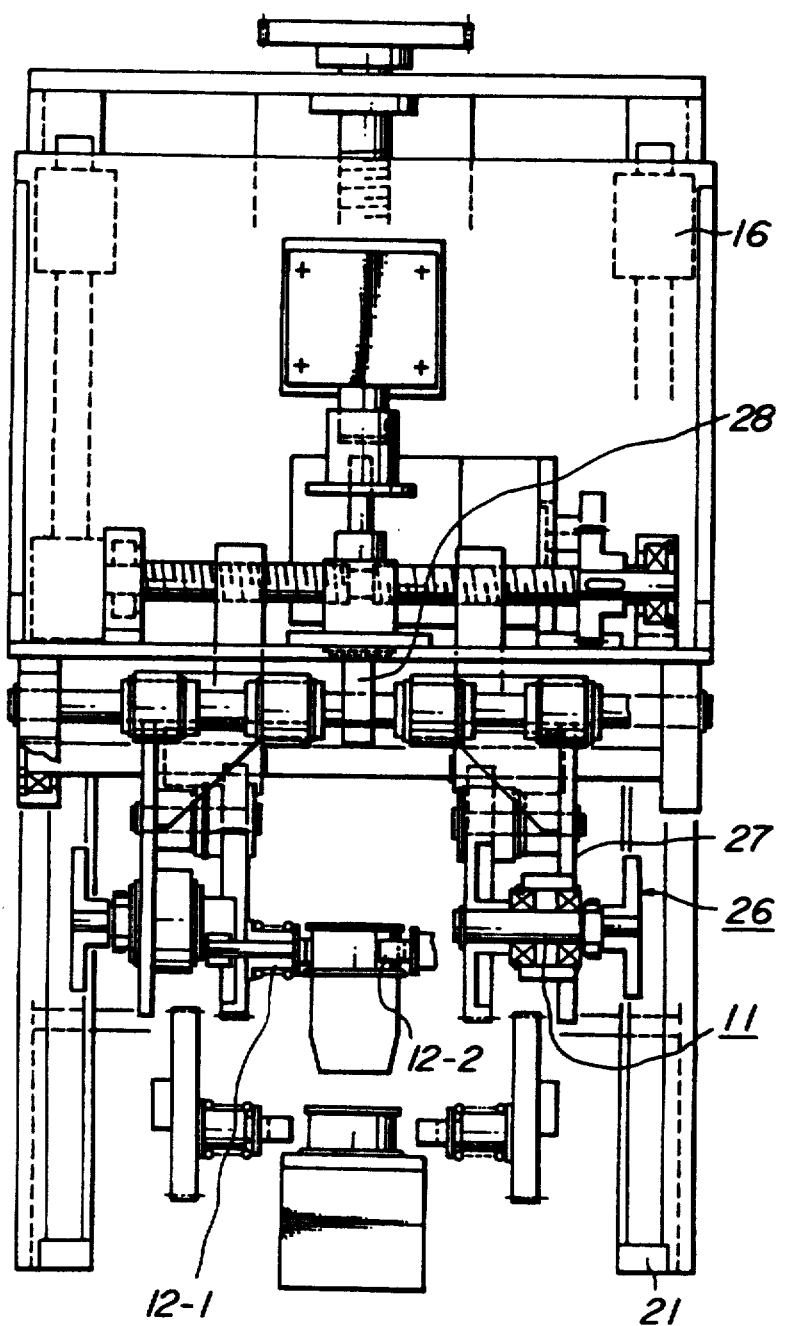
FIG. 4 is a side view of the material vessel transferring unit.

FIGS. 3 and 4 illustrate in front and side views one example of the material vessel transferring unit 3 of the material supply unit. In the embodiment shown in FIGS. 3 and 4, the material vessel transferring unit 4 comprises grasping means 11, a lifter 16, transfer means 21 and turn-over introducing means 26. The grasping means 11 embraces and holds the material vessel 7 by supports 12-1 and 12-2 on both sides. The lifter 16 raises and lowers the material vessel 7, embraced by the grasping means 11. The lifter 16 is raised or lowered by a motor 18 which drives ball screws 17 to raise or lower nuts 19 engaged with the ball screws 17. The transfer means 21 translately moves, relative to the base 5, along guides provided on the base 5. The turn-over introducing means 26 comprises a turn-over mechanism 27 for turning over the embraced material vessel by 180°, and an introducing mechanism 28 for striking a bottom of the material vessel 7 once or twice to remove the congregated material at the inside of the bottom from the vessel.

The material vessel transferring unit 3 described above is moved by the transfer means 21 to a position of the predetermined material vessel 7 in the material rack 6 1 at the material introducing position. Then the material vessel transferring unit 3 is lowered to the position of the material vessel 7 where the vessel 7 is embraced by the grasping means 11. The material vessel transferring unit 3 is then once raised embracing the vessel 7 by the lifter 16. Thereafter, the transferring unit 3 is transferred by the transfer means 21 to the material introducing port of the automatic crusher 1. From this position, the unit 3 is lowered by the lifter 16 to the proximity of the material introducing port, and thereafter the unit 3 is turned over through 180° by the turn-over mechanism 27 of the turn-over introducing means 26. Finally, the introducing mechanism 28 strikes once or twice the bottom of the material vessel 7 to supply the remaining congregated material at the inside of the bottom into the material introducing port. The material supplying operation is completed in this manner. Moreover, all the operations above described are effected by control of the control means 8.

As can be seen from the above explanation, the material supply apparatus supplies material by controlling the operations of the material vessel pooling unit and the material vessel transferring unit by the control means. Therefore, a predetermined order of the operations is previously inputted in the control means so that desired materials can be selectively introduced into a required apparatus. Moreover, the introduction of the material can be effected automatically and exactly.

Figure 5:
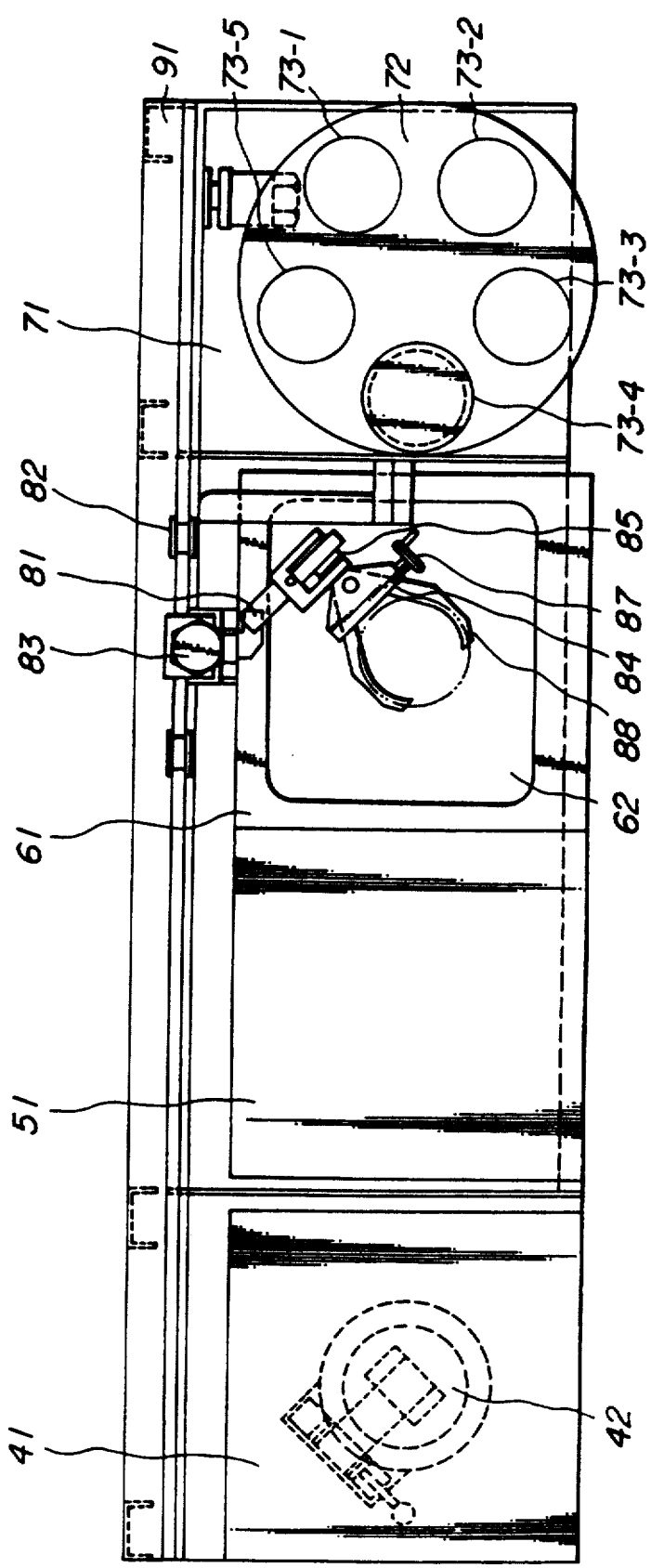
FIG. 5 is a plan view illustrating one example of a crushing system according to the invention.
Figure 6:
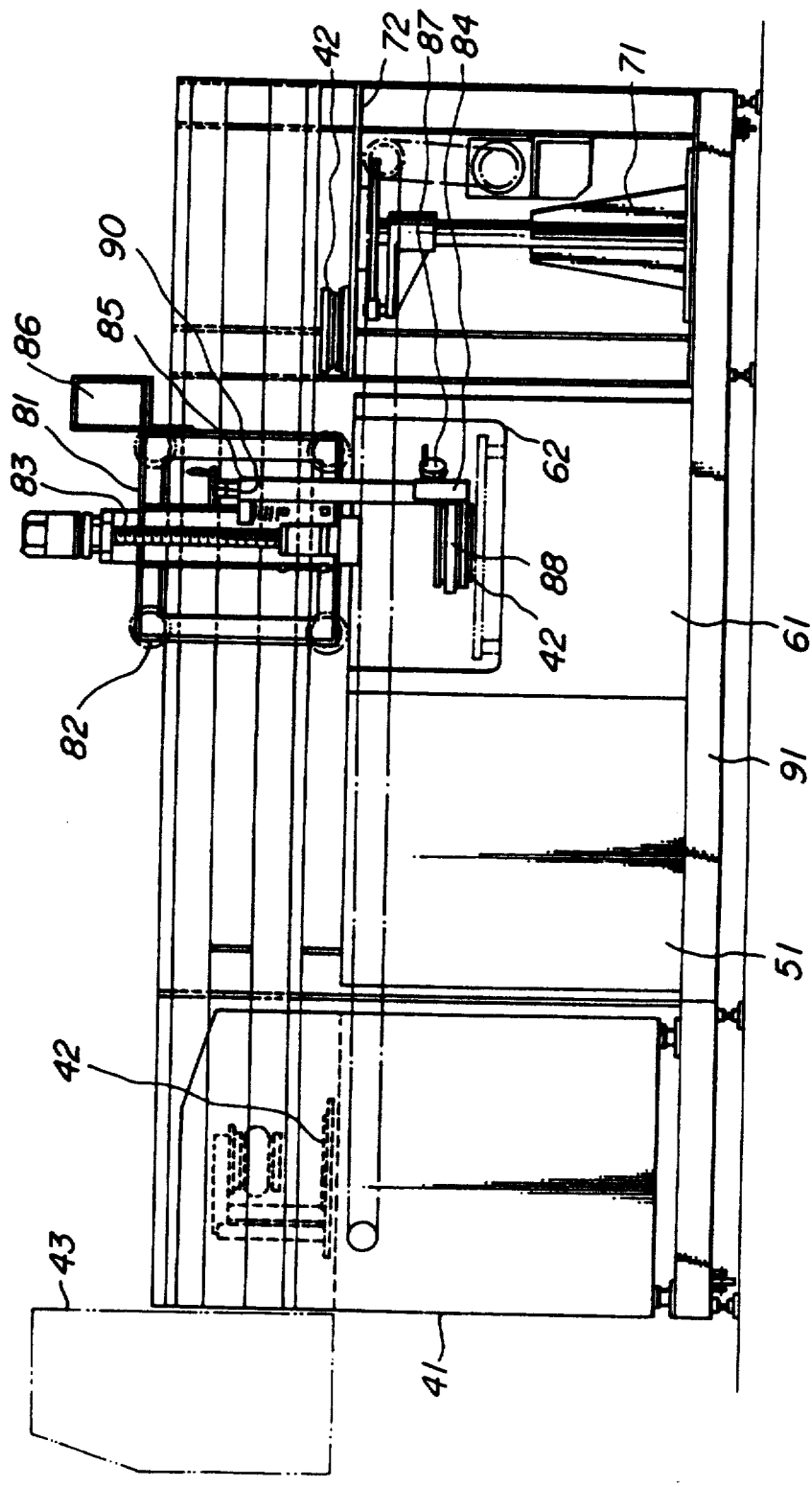
FIG. 6 is a front elevation of the crushing system as shown in FIG. 5.

FIGS. 5 and 6 are plan and front views illustrating one example of the crushing system having a crushing vessel transferring unit according to the invention. In this embodiment, the crushing system comprises on a base 91 a manual crusher 41, a working table 51, a crushing vessel cleaning unit 61, a crushing vessel stocker 71 and the crushing vessel transferring unit 81.

The manual crusher 41 is commercially available in this embodiment. After a crushing vessel 42 holding samples to be crushed therein has been arranged at a predetermined position in the manual crusher 41, the crusher 41 is closed by a cover 43 and the vessel 42 therein is restrained by an air bag (not shown). Thereafter, the crusher is vibrated by rotation of a motor to crush the samples in the vessels in the crusher. Loading of the crushing vessel 42 into the crusher 41 is carried out by the use of the crushing vessel transferring unit 81.

Figure 8A:
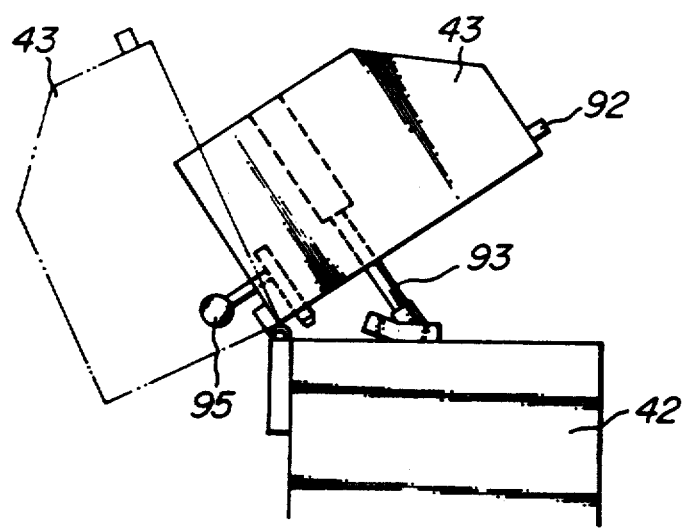
FIGS. 8a and 8b are side and plan views illustrating a cover and a crushing vessel for the crushing system, which is provided with safety devices for the operation.
Figure 8B:
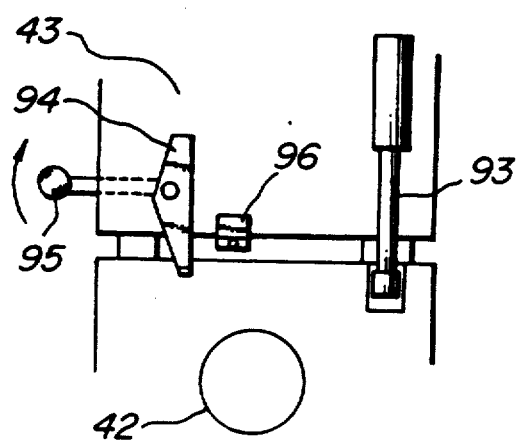

With the manual crusher 41 in this embodiment are particular safety devices associated with the cover 43. Referring to FIGS. 8a and 8b illustrating the cover 43 and the crushing vessel 42, respectively, in front and plan views. The cover 43 is manually opened by one hand of an operator gripping a grip 92. In this case, the cover 43 is slowly moved by an action of a hydraulic shock damper 93. When the cover approaches the vessel 42, a cover support mechanism 94 butts against the vessel 42 so that the closing of the cover 43 is prevented. Therefore, the operator grips a lever by his other hand and pushes the lever as shown by an arrow in FIG. 8b to disengage the cover support mechanism 94 from the engagement with the vessel 42. In order to close the cover, it is absolutely necessary for the operator to manipulate the grip 92 by one hand and lever 95 by another hand so that the operator does not unintentionally clamp his hand between the cover 43 and vessel 42. Therefore, the hydraulic shock damper and the cover support mechanism 44 having the lever 95 form a safety device for the operation. Moreover, the cover 43 is provided with a microswitch 96 such as a contactless switch. When the cover 43 is completely closed, the microswitch 96 causes a power source for the crushing vessel 42 to turn on so that the crushing vessel 42 starts to operate after closing the cover 43 without fail. Such a microswitch 96 also forms a safety device.

On the working table 51 is arranged the crushing vessel 42 which has been clamped by the crushing vessel transferring unit 81 and transferred from the manual crusher 41 or crushing vessel cleaning unit 61. For this purpose, a height of the table 51 is substantially equal to heights of the manual crusher 41 and the crushing vessel cleaning unit 61.

The crushing vessel cleaning unit 61 used for washing and cleaning the crushing vessels 42 is constructed for this purpose such that the crushing vessel 42, held by the crushing vessel transferring unit 81, is cleaned by water and alcohol in a scullery or sink 62 made of stainless steel. In other words, the crushing vessel 42 which has been transferred thereto by the crushing vessel transferring crusher 41 is arranged in the scullery or sink 62 wherein the vessel 42 is cleaned with water by nylon scrubbing brushes or the like and washed with alcohol, thereby removing from the inside of the vessel 42 samples crushed in previous crushing processes which remain in the vessel 42.

The crushing vessel stocker 71 is used to dry the cleaned vessels 42 arranged thereon to prepare the vessels 42 for the next use. The stocker 71 comprises a manually rotatable turn-table 72 on which five crushing vessels 42 are held. Positioning of the turn-table 72 in its manual rotation is effected by click stops corresponding to five vessel holder 73-1 to 73-5.

The crushing vessel transferring unit 81 moves together with the crushing vessel 42 held thereby between the manual crusher 41, the working table 51 and the crushing vessel cleaning unit 61. The crushing vessel transferring unit 81 in this embodiment comprises: a traverse feeding mechanism 82 capable of rough movements and fine movements for positioning, a lifting mechanism 83 for raising and lowering the crushing vessel 42, a clamping mechanism 84 for clamping the crushing vessel 42, a tilting mechanism 85 for tilting the crushing vessel 42, and a control board 86 for instructing and controlling operations of the traverse feeding mechanism 82, lifting mechanism 83 and tilting mechanism 85.

The traverse feeding mechanism 82 is so constructed as to enable the crushing vessel 42 to move in a rough movement to a desired position or the proximity of the desired position with the aid of an electric motor according to an instruction by pushing a switch of the control board 86. Moreover, the traverse feeding mechanism 82 is so constructed that after the rough movement, the crushing vessel 42 is manually moved in a fine movement to achieve an exact positioning of the vessel 42 in a case as the crushing vessel 42 is loaded into the manual crushing vessel 41 and crushing vessel stocker 71. The lifting mechanism 83 serves to raise or lower the crushing vessel 42 which has been transferred to the desired transferred position by operation of a switch of the control board, thereby moving the crushing vessel to or from a predetermined position. When the crushing vessel 42 is raised to the uppermost position or lowered to the lowermost position in the scullery 62 of the crushing vessel cleaning unit 61, the raising or lowering movement is stopped by a limit switch (not shown) for the upper or lower limit. The clamping mechanism 84 is constructed such that by rotating a clamping wheel 87, clamp levers 48 are adjusted to clamp the crushing vessel 42 securely. There are two kinds of crushing vessels 42 according to amounts of samples to be crushed in this embodiment shown in FIG. 7. The clamp levers 88 are formed in their insides with grooves 89. In the case of a smaller crushing vessel 42, as shown on the left in FIG. 7, the vessel 42 is clamped by the insides of the clamp levers 88 except the grooves 89. On the other hand, a larger crushing vessel 42, as shown on the right in FIG. 7, is clamped by the inside of the grooves 89 of the clamp levers 88. Therefore, one kind of clamp levers can clamp two kinds of crushing vessels in this manner. The tilting mechanism 85 serves to tilt the crushing vessel 42 to assist the cleaning operation by water. The crushing vessel 42 can be tilted at any angle by rotating a tilting wheel 90 which is preferably made of stainless steel, resistant to rust.

The invention is not limited to the embodiment and various changes and modification may be made in the invention. For example, although the five crushing vessels have been held on the turn-table 32, many vessels more than five may, of course, be held on the table.

As can be seen from the above explanation, according to the crushing system having the crushing vessel transferring unit of the invention, the transference of the crushing vessels between the manual crusher, working table, cleaning unit and crushing vessel stocker is carried out by the crushing vessel transferring unit. Therefore, the heavy crushing vessels are automatically transferred without using manual operation, but the operations of introduction and removal of samples and cleaning of the vessels are manually effected, whose manual operations are preferable. Accordingly, the crushing operation of samples can be carried out in safety with high efficiency.

FIGS. 9 and 10 are plan and front views illustrating one example of the analysis sample transferring apparatus together with a fluorescent X-ray analyzing apparatus. In this embodiment, the analysis sample transferring apparatus is provided between an automatic press 101 and a fluorescent X-ray analyzing apparatus 102. The analysis sample transferring apparatus comprises: a formed sample transferring unit 103 for transferring and temporarily storing formed samples, a formed sample loading and unloading unit 104 for loading and unloading a formed sample into and out of a predetermined holder and loading and unloading the loaded and unloaded holder into and out of a holder tray, formed sample delivery unit 105 for transferring the formed samples between the formed sample transferring unit 103 and the formed sample loading and unloading unit 104, a holder tray transferring unit 106 for transferring the holder tray to a predetermined position, and a standard sample storing and lifting unit 107.

In this embodiment, the formed sample 112, transferred to a formed sample removing opening 111 of the automatic press 101 by elevating means (not shown), is supplied to a rail-like pool 113 of the formed sample transferring unit 103 and are stored therein if required. The formed sample 112 arrived at an end of the pool 113 is held by a formed sample delivery unit 105 and rotated under this condition into a position shown by phantom lines in FIG. 9. In the formed sample loading and unloading unit 104 at a position of the rotated formed sample 112, the formed sample 112 is loaded into the holder 115 previously arranged in the holder tray 114 by a clamp built-in spindle (not shown). After loading formed sample 112 into six holders 115, the holder tray 114 is transferred by the holder tray transferring unit 106 to a predetermined position in front of a sample loader 116 of the fluorescent X-ray analyzing apparatus 102. The holder 115 loaded with the formed sample 112 therein is supplied one by one to the fluorescent X-ray analyzing apparatus 102 to be analysis. After analyzed, the formed samples 112 are returned together with the holders 115 to the holder tray 114 and further transferred to the formed sample loading and unloading unit 104 by the holder tray transferring unit 106. The analyzed formed samples 112 are removed one by one from the holder 115 by means of the formed sample loading and unloading unit 104. Thereafter, the formed samples 112 are fed by the formed sample delivery unit 105 through introducing chute 17-1 or 17-2 into sample storing cases 118 and stored therein.

Before starting usual analyzing operations, the fluorescent X-ray analyzing apparatus 102 must be calibrated with calibration curves or apparatus itself. For this purpose, the reference sample storing and lifting unit 107 (for storing reference samples) is provided in a transferring path of the holder tray 114 so that reference samples 119 can be supplied to the fluorescent X-ray analyzing apparatus 102 as the case may be. The reference sample storing and lifting unit 107 is constructed such that eight trays 120, each supporting six reference sample at the most, can be accommodated therein.

FIGS. 11a, 11b and 11c are sectional and bottom plan views of the holder 115 and a sectional view of the clamp built-in spindle 121. FIG. 11a illustrates the holder 115 and the formed sample 112 therein. In more detail, a holder body 122 is formed integrally with a mask 123 and a plastic insert 124 to form a holder body unit. A movable lock plate 125 supporting thereon the formed sample 112, a spring 126 and a spring anchoring member 127 form a locking unit. The locking unit is inserted into the holder body unit so that pawls 129 of the lock plate 125 are urged against notches 128 of the holder body 122, thereby holding the formed sample 112 to the holder 115. As shown in FIG. 11b, the lock plate 125 is provided on its bottom with a clamp engaging portion 130 and two position detecting apertures 131-1 and 131-2. The clamp built-in spindle 121 comprises movable clamp 133 and a diffused reflection type photoelectric switch 134 arranged in a spindle member 132 as shown in section in FIG. 11c.

The loading and unloading operation of the formed sample 112 using the holder 115 and the clamp built-in spindle 121 will be explained. The holder 115 supporting the analyzed formed sample 112 is transferred by the holder tray 114 to the center of the formed sample loading and unloading unit 104 and stopped thereat. In this position, the clamp built-in spindle 121 is raised from below and once stopped immediately before a tip end of the spindle 121 contacts the movable lock plate 125. At the same time, the spindle 121 is slowly rotated as a whole so that a position at which the holder body 122 is to be clamped is determined with the aid of the photoelectric switch 134 and the position detecting apertures 131-1 and 131-2. Thereafter, the spindle 121 in its entirety supporting on the tip end the holder 115, is further raised, while being slowly rotated. The spindle 121 is then stopped at the position of the holder clamp mechanism of the formed sample loading and unloading unit 104 to clamp the holder body 122. Under this condition, the clamp 133 in the spindle 121 is actuated to disengage the pawls 129 of the movable lock plate 125 from the notches 128 of the holder body 122. Thereafter, the spindle 121 is lowered together with the lock plate 125 and the formed sample 112 thereon so that the formed sample 112 is exchanged with a new formed sample 112 by means of the formed sample transfer means 105. The new formed sample 112 is then accommodated in the holder body 122. The complete loading of the formed body 112 in the holder body 122 is ascertained by detecting the positions of the pawls 129 of the movable lock plate 125 by means of the photoelectric switch 134.

As can be seen from the above explanation, the analysis sample transferring apparatus, according to the invention, is capable of automatically transferring formed samples so that formed samples for the analysis can be automatically transferred to a predetermined analyzing apparatus without requiring manual operation. Moreover, as the reference sample storing and lifting unit is added to the holder tray transferring unit, calibration lines or calibration of an analyzing apparatus in analyzing various kinds of samples can easily be effected so that precise analyzing can be carried out.

FIG. 12 is a plan view illustrating one example of the fluorescent X-ray analyzing system according to the invention. In this embodiment, a sample is crushed to a predetermined grain size in an automatic crusher 151 and the crushed sample is then transferred to an automatic press 153 by a crushed sample transferring unit 152. The crushed sample is formed into predetermined shapes such as disks in the automatic press 153, and the formed samples are supplied by a formed sample supply unit 154 to a fluorescent X-ray analyzing apparatus 155 through a partition wall separating the fluorescent X-ray analyzing apparatus 155 and a pretreating unit including an automatic crusher 151 and the automatic press 153. The formed samples supplied to the analyzing apparatus 155 are once stored if required and thereafter are loaded in a holder in a sample loader 159 by means of a holder loading and unloading unit 158. Thereafter, the samples are set in the fluorescent X-ray analyzing apparatus 155 by an action of the sample loader 159 for carrying out the X-ray fluorescence analysis. Operations of the automatic crusher 151, crushed sample transferring unit 152, automatic press 153, formed sample supply unit 154, sample transfer pooling unit 157, holder loading and unloading unit 158, sample loader 159 and fluorescent X-ray analyzing apparatus 155 are controlled by control means 160. The control means 160 comprises usual computers.

FIGS. 13 and 14 are plan and side views illustrating an upper construction of the automatic crusher 151 in the fluorescent X-ray analyzing system according to the invention. As shown in these drawings, at the upper portion of the automatic crusher, a first cup pooling unit 171 and a sample introducing unit 172 are provided on a base 173 for selecting particular samples from various kinds of samples and introducing them into the automatic crusher 151. In more detail, the first cup pooling unit 171 comprises sample racks 174-1 to 174-8, each including ten sample cups 175. There are totally sample cups 175. Before starting the operation, positions and kinds of the eighty sample cups are inputted into the control means 160, on the basis of which inputted data the crushing is actually effected. The first cup pooling unit 171 is able to move in both directions as shown by an arrow so that a rack or rack 174-1 in this embodiment positioned at a rack moving position a is transferred to a sample introducing position shown in the drawing. The sample in the sample cup 175 at the sample introducing position is held and transferred together with the sample cup 175 by a cup grasping unit 176 of the sample introducing unit 172 in a predetermined order so as to be introduced into a sample introducing opening of the automatic crusher 151 by an action of the cup grasping unit 126.

The crushed samples are supplied from a sample exhaust opening 177 of the automatic crusher 151 to a crushed sample cup 179 of crushed sample pooling unit 178 as second cup pooling unit of the crushed sample transferring unit 152 as shown in FIG. 14. The crushed sample cups 179 are transferred in desired timing to a position of a cup loading and unloading unit 180 by means of the crushed sample pooling unit 178. The crushed samples are weighed by an electronic balance 186 if required. The cup 179 is held by the cup loading and unloading unit 180, while a cup transferring unit 182 is transferred to the position of the cup loading and unloading unit 180. The cup 179 is held by grasping means 183 of the unit 180 and then supplied to the automatic press 153.

If the sample is a ceramic, it must be crushed to a size of the order of mean diameter of about 0.3 $\mu$m in order to effect the X-ray fluorescence analysis with high accuracy. In the present system, the sample is added with a crushing aid and crushed under a dried condition. The automatic crusher 151 and the automatic press 153 may be commercially available ones. For example, Model HSM-F36 (HERZOG Company) and the like are preferably used as the automatic crusher for the embodiment. Moreover, in the automatic press 153, supplied sample powder is pressed in a predetermined ring which can be loaded in a sample holder of the fluorescent X-ray analyzing apparatus 155 to form a formed sample 185 which is removed through a formed sample removing opening 34. The automatic press 153 includes an analyzed sample supply means (not shown) for punching measured samples and recovering the forming rings.

Moreover, the fluorescent X-ray analyzing system includes an analysis sample transferring apparatus. Such an apparatus is substantially the same as that shown in FIGS. 9 and 10, and a holder and a clamp built-in spindle are also substantially the same as those shown in FIGS. 11a, 11b and 11c.

The arrangement of the automatic crusher, automatic press and fluorescent X-ray analyzing apparatus is not limited to that shown in the above embodiment. All that is required is an effective connection of these apparatuses.

The fluorescent X-ray analyzing system according to the invention uses the automatic crusher capable of selecting various kinds of samples and crushing them, so that various kinds of samples can be continuously and automatically analyzed. Moreover, the crushed sample transferring unit and the formed sample supply unit connect between the automatic crusher, automatic press and fluorescent X-ray analyzing apparatus. Operations of these components are controlled by the control means. Therefore, automatization of the system and saving power can be accomplished.

It is further understood by those skilled in the art that the foregoing description is that of preferred embodiments of the disclosed invention and that various changes and modifications may be made in the invention without departing from the spirit and scope thereof.

What is claimed is:

1. A crushing system having a crushing vessel transferring unit comprising:
    a manual crusher for crushing a sample in a crushing vessel;
    a working table for introducing the sample into the crushing vessel and removing a crushed sample from the crushing vessel;
    a crushing vessel cleaning unit for cleaning the crushing vessel from which the crushed sample has been removed;
    a crushing vessel stocker for storing cleaned crushing vessels; and
    a crushing vessel transferring unit for transferring the crushing vessels between the manual crusher, the working table, the crushing vessel cleaning unit and the crushing vessel stocker.

2. A crushing system as set forth in claim 1, wherein said crushing vessel transferring unit comprises:
    a traverse feeding mechanism for performing said transferring of the crushing vessels;
    a lifting mechanism for raising and lowering the crushing vessels;
    a clamping mechanism for clamping the crushing vessels;
    a tilting mechanism for tilting the crushing vessels; and
    a control board for instructing operations of the above mechanisms.

3. A crushing system as set forth in claim 1, wherein said crushing vessel has a safety device which comprises: closing speed slow-down means for causing a cover for said vessel to close slowly and a cover support mechanism which stops said cover approaching said vessel and is manually operated to allow the cover to close.

4. A crushing system as set forth in claim 1, wherein said crushing vessel has a safety device which comprises a microswitch which is actuated when a cover of said vessel is completely closed to cause the vessel to operate.

* * * * *